United States Patent [19]
Yager et al.

[11] Patent Number: 5,716,852
[45] Date of Patent: Feb. 10, 1998

[54] MICROFABRICATED DIFFUSION-BASED CHEMICAL SENSOR

[75] Inventors: Paul Yager; Bernhard H. Weigl; James P Brody; Mark R. Holl, all of Seattle, Wash.

[73] Assignee: University of Washington, Seattle, Wash.

[21] Appl. No.: 625,808

[22] Filed: Mar. 29, 1996

[51] Int. Cl.⁶ .................................................. G01N 21/64
[52] U.S. Cl. ........................... 436/172; 436/177; 436/180; 422/81
[58] Field of Search ........................ 436/172, 177, 436/180, 52; 422/81, 82, 82.08

[56] References Cited

U.S. PATENT DOCUMENTS

| | | | |
|---|---|---|---|
| 3,449,938 | 6/1969 | Giddings | 73/23 |
| 4,147,621 | 4/1979 | Giddings | 210/22 C |
| 4,214,981 | 7/1980 | Giddings | 209/155 |
| 4,250,026 | 2/1981 | Giddings et al. | 209/155 |

(List continued on next page.)

FOREIGN PATENT DOCUMENTS

| | | | |
|---|---|---|---|
| 0 645 169 A1 | 3/1995 | European Pat. Off. | B01D 21/00 |

OTHER PUBLICATIONS

Faucheux, L.P., et al. (1995), "Optical Thermal Ratchet," Physical Rev. Letters 74:1504–1507.

Giddings, J.C. (1985), "Optimized Field–Flow Fractionation System Based on Dual Stream Splitters," Anal. Chem. 57:945–947.

Giddings, J.C., et al. (1983), "Outlet Stream Splitting for Sample Concentration in Field–Flow Fractionation," Separation Science and Technology 18:293–306.

(List continued on next page.)

*Primary Examiner*—Jeffrey Snay
*Attorney, Agent, or Firm*—Greenlee, Winner and Sullivan, P.C.

[57] ABSTRACT

A channel-cell system is provided for detecting the presence and/or measuring the presence of analyte particles in a sample stream comprising: a) a laminar flow channel; b) two inlet means in fluid connection with said laminar flow channel for respectively conducting into said laminar flow channel (1) an indicator stream which may comprise an indicator substance which indicates the presence of said analyte particles by a detectable change in property when contacted with said analyte particles, and (2) said sample stream; c) wherein said laminar flow channel has a depth sufficiently small to allow laminar flow of said streams and a length sufficient to allow particles of said analyte to diffuse into said indicator stream to the substantial exclusion of said larger particles in said sample stream to form a detection area; and d) outlet means for conducting said streams out of said laminar flow channel to form a single mixed stream.

19 Claims, 3 Drawing Sheets

U.S. PATENT DOCUMENTS

| | | | |
|---|---|---|---|
| 4,683,212 | 7/1987 | Uffenheimer | 436/52 |
| 4,737,268 | 4/1988 | Giddings | 209/12 |
| 4,830,756 | 5/1989 | Giddings | 210/739 |
| 4,894,146 | 1/1990 | Giddings | 209/12 |
| 5,019,515 | 5/1991 | Gisin et al. | 436/52 |
| 5,039,426 | 8/1991 | Giddings | 210/695 |
| 5,141,651 | 8/1992 | Giddings | 210/748 |
| 5,156,039 | 10/1992 | Giddings | 73/1 R |
| 5,193,688 | 3/1993 | Giddings | 209/155 |
| 5,240,618 | 8/1993 | Caldwell et al. | 210/748 |
| 5,389,524 | 2/1995 | Larsen et al. | 436/52 |
| 5,465,849 | 11/1995 | Wada et al. | 209/214 |

OTHER PUBLICATIONS

Giddings, J.C. (1993), "Field–Flow Fractionation: Analysis of Macromolecular, Colloidal and Particulate Materials," Science 260:1456–1465.

Leff, H.S. and Rex, A.F. (1990), "Resource letter MD–1: Maxwell's demon." Am. J. Physics 58:201–209.

Reisman, A., et al., "The Controlled Etching of Silicon in Catalyzed Ethylenediamine–Pyrocatechol–Water Solutions," (1979) J. Electrochem. Soc. 126:1406–1415.

Rousselet, J., et al. (1994), "Directional motion of brownian particles induced by a periodic asymmetric potential," Nature 370:446–448.

Shoji, S. and Esashi, M. (1994), "Microflow devices and systems," J. Micromechanics and Microengineering, 4:157–171.

Wallis, G. and Pomerantz, D.I, "Field Assisted Glass–Metal Sealing," (1969) J. Appl. Physics 40:3946–3949.

Williams, P.S., et al. (1992), "Continuous SPLITT Fractionation Based on a Diffusion Mechanism," Ind. Eng. Chem. Res. 31:2172–2181.

MICROFABRICATED DIFFUSION-BASED CHEMICAL SENSOR

This invention was made with government support under Army research contract DAMD17-94-J-4460 awarded by the U.S. Army. The government has certain rights in the invention.

FIELD OF THE INVENTION

This invention relates generally to microsensors and methods for analyzing the presence and concentration of small particles in streams containing both these small particles and larger particles by diffusion principles. The invention is useful, for example, for analyzing blood to detect the presence of small particles such as hydrogen, sodium or calcium ions in a stream containing cells.

BACKGROUND OF THE INVENTION

In Maxwell's famous gedanken (thought) experiment, a demon operates a door between two boxes of gas at the same temperature. The demon sorts the molecules keeping the faster molecules in one box and the slower in the other, violating the basic laws of thermodynamics. This paradox has since been resolved in many different ways. Leff, H. S. and Rex, A. F. (1990), "Resource letter md-1: Maxwell's demon," Am. J. Physics 58:201–209.

A similar arrangement can be used to separate particles. Consider a mixture of particles of two different sizes suspended in water in one box and pure water in the other. If the demon opens and closes the door between the boxes quickly enough so that none of the larger particles have time to diffuse through the doorway, but long enough so that some of the smaller particles have enough time to diffuse into the other box, some separation will be achieved.

Recently two experiments have been done where a spatially asymmetric potential is periodically applied in the presence of a number of brownian particles. Faucheux, L. S., et al. (1995), "Optical thermal ratchet," Physical Rev. Letters 74:1504–1507; Rousselet, J., et al. (1994), "Directional motion of brownian particles induced by a periodic asymmetric potential," Nature 370:446–448.

This has been shown to lead to a directed motion of the particles at a rate depending on the diffusion coefficient. One experiment (Rousselet, J., et al. (1994), "Directional motion of brownian particles induced by a periodic asymmetric potential," Nature 370:446–448) used microfabricated electrodes on a microscope slide to apply an electric field for the potential. This idea is also the subject of European Patent Publication 645169 of Mar. 29, 1995, for "Separation of particles in a fluid—using a saw-tooth electrode and an intermittent excitation field," Adjari, A., et al. The other experiment (Faucheux, L. S., et al. (1995), "Optical thermal ratchet," Physical Rev. Letters 74:1504–1507) used a modulated optical tweezer arrangement.

Diffusion is a process which can easily be neglected at large scales, but rapidly becomes important at the microscale. The average time t for a molecule to diffuse across a distance d is $t=d^2/D$ where D is the diffusion coefficient of the molecule. For a protein or other large molecule, diffusion is relatively slow at the macro-scale (e.g. hemoglobin with D equal to $7\times10^{-7}$ cm$^2$/s in water at room temperature takes about $10^6$ seconds (ten days) to diffuse across a one centimeter pipe, but about one second to diffuse across a ten micron channel).

Using tools developed by the semiconductor industry to miniaturize electronics, it is possible to fabricate intricate fluid systems with channel sizes as small as a micron. These devices can be mass-produced inexpensively and are expected to soon be in widespread use for simple analytical tests.

A process called "field-flow fractionation" (FFF) has been used to separate and analyze components of a single input stream in a system not made on the microscale, but having channels small enough to produce laminar flow. Various fields, including concentration gradients, are used to produce a force perpendicular to the direction of flow to cause separation of particles in the input stream. See, e.g. Giddings, J. C., U.S. Pat. No. 3,449,938, Jun. 17, 1969, "Method for Separating and Detecting Fluid Materials;" Giddings, J. C., U.S. Pat. No. 4,147,621, Apr. 3, 1979, "Method and Apparatus for Flow Field-Flow Fractionation;" Giddings, J. C., U.S. Pat. No. 4,214,981, Jul. 29, 1980), "Steric Field-Flow Fractionation;" Giddings, J. C., et al., U.S. Pat. No. 4,250,026, Feb. 10, 1981, "Continuous Steric FFF Device for The Size Separation of Particles;" Giddings, J. C., et al., (1983), "Outlet Stream Splitting for Sample Concentration in Field-Flow Fractionation," Separation Science and Technology 18:293–306; Giddings, J. C. (1985), "Optimized Field-Flow Fractionation System Based on Dual Stream Splitters," Anal. Chem. 57:945–947; Giddings, J. C., U.S. Pat. No. 4,830,756, May 16, 1989, "High Speed Separation of Ultra-High Molecular Weight Polymers by Hyperlayer Field-Flow Fractionation;" Giddings, J. C., U.S. Pat. No. 4,141,651, Aug. 25, 1992, "Pinched Channel Inlet System for Reduced Relaxation Effects and Stopless Flow Injection in Field-Flow Fractionation;" Giddings, J. C., U.S. Pat. No. 5,156,039 Oct. 20, 1992, "Procedure for Determining the Size and Size Distribution of Particles Using Sedimentation Field-Flow Fractionation;" Giddings, J. C., U.S. Pat. No. 5,193,688, Mar. 16, 1993, "Method and Apparatus for Hydrodynamic Relaxation and Sample Concentration in Field-Flow Fraction Using Permeable Wall Elements;" Caldwell, K. D. et al., U.S. Pat. No. 5,240,618, Aug. 31, 1993, "Electrical Field-Flow Fractionation Using Redox Couple Added to Carrier Fluid;" Giddings, J. C. (1993), "Field-Flow Fractionation: Analysis of Macromolecular, Colloidal and Particulate Materials," Science 260:1456–1465; Wada, Y., et al., U.S. Pat. No. 5,465,849, Nov. 14, 1995, "Column and Method for Separating Particles in Accordance with their Magnetic Susceptibility." None of these references disclose the use of a separate input stream to receive particles diffused from a particle-containing input stream.

A related method for particle fractionation is the "Split Flow Thin Cell" (SPLITT) process. See, e.g., Williams, P. S., et al. (1992), "Continuous SPLITT Fractionation Based on a Diffusion Mechanism," Ind. Eng. Chem. Res. 31:2172–2181; and J. C. Giddings U.S. Pat. No. 5,039,426. These publications disclose channel cells with channels small enough to produce laminar flow, but again only provide for one inlet stream. A further U.S. patent to J. C. Giddings, U.S. Pat. No. 4,737,268, discloses a SPLITT flow cell having two inlet streams (FIG. 3); however the second inlet stream is not an indicator stream, but rather a particle-free stream. Giddings U.S. Pat. No. 4,894,146 also discloses a SPLITT flow cell having two input streams, but no indicator stream. All these SPLITT flow methods require the presence of more than one output stream for separating various particle fractions.

None of the foregoing publications describe a channel system capable of analyzing small particles in very small quantities of sample containing larger particles, particularly larger particles capable of affecting the indicator used for the analysis. No devices or methods using indicator streams within the cell system are described.

SUMMARY OF THE INVENTION

Microfluidic devices allow one to take advantage of diffusion as a rapid separation mechanism. Flow behavior in microstructures differs significantly from that in the macroscopic world. Due to extremely small inertial forces in such structures, practically all flow in microstructures is laminar. This allows the movement of different layers of fluid and particles next to each other in a channel without any mixing other than diffusion. On the other hand, due to the small lateral distances in such channels, diffusion is a powerful tool to separate molecules and small particles according to their diffusion coefficients, which are usually a function of their size.

This invention provides a channel cell system for detecting the presence of analyte particles in a sample stream also comprising larger particles comprising:

a) a laminar flow channel;

b) at least two inlet means in fluid connection with said laminar flow channel for respectively conducting into said laminar flow channel (1) an indicator stream, said indicator stream preferably comprising an indicator substance, for example, a pH-sensitive dye, which indicates the presence of said analyte particles by a detectable change in property when contacted with said analyte particles, and (2) said sample stream;

c) wherein said laminar flow channel has a depth sufficiently small to allow laminar flow of said streams adjacent to each other and a length sufficient to allow analyte particles to diffuse into said indicator stream to the substantial exclusion of said larger particles in said sample stream to form a detection area;

d) outlet means for conducting said streams out of said laminar flow channel to form a single mixed stream.

In the simplest embodiment of this invention, a single indicator stream and a single sample stream are used; however, the methods and devices of this invention may also use multiple sample and/or indicator streams, and reference or calibration streams, all in laminar flow with each other.

The preferred embodiments of this invention utilize liquid streams, although the methods and devices are also suitable for use with gaseous streams.

The term "detection" as used herein means determination that a particular substance is present. The methods and apparatuses of this invention can also be used to determine the concentration of a substance in a sample stream.

The channel cell system of this invention may comprise external detecting means for detecting changes in an indicator substance carried within the indicator stream as a result of contact with analyte particles. Detection and analysis is done by any means known to the art, including optical means, such as optical spectroscopy, and other means such as absorption spectroscopy or fluorescence, by chemical indicators which change color or other properties when exposed to the analyte, by immunological means, electrical means, e.g. electrodes inserted into the device, electrochemical means, radioactive means, or virtually any microanalytical technique known to the art including magnetic resonance techniques, or other means known to the art to detect the presence of an analyte such as an ion, molecule, polymer, virus, DNA sequence, antigen, microorganism or other factor. Preferably optical or fluorescent means are used, and antibodies, DNA sequences and the like are attached to fluorescent markers.

The term "particles" refers to any particulate material including molecules, cells, suspended and dissolved particles, ions and atoms.

The input stream may be any stream containing particles of different size, for example blood, contaminated drinking water, contaminated organic solvents, urine, biotechnological process samples, e.g. fermentation broths, and the like. The analyte may be any smaller particle in the input stream which is capable of diffusing into the indicator stream in the device, e.g. hydrogen, calcium or sodium ions, proteins, e.g. albumin, organic molecules, drugs, pesticides, and other particles. In the preferred embodiment when the sample stream is whole blood, small ions such as hydrogen and sodium diffuse rapidly across the channel, whereas larger particles such as those of large proteins, blood cells, etc. diffuse slowly. Preferably the analyte particles are no larger than about 3 micrometers, more preferably no larger than about 0.5 micrometers, or are no larger than about 1,000,000 MW, and more preferably no larger than about 50,000 M.W.

The system may also include an indicator stream introduced into one of the inlet means comprising a liquid carrier containing substrate particles such as polymers or beads having an indicator substance immobilized thereon. The liquid carrier can be any fluid capable of accepting particles diffusing from the feed stream and containing an indicator substance. Preferred indicator streams comprise water and isotonic solutions such as salt water with a salt concentration of about 10 mM NaCl, KCl or MgCl, or organic solvents like acetone, isopropyl alcohol, ethanol, or any other liquid convenient which does not interfere with the effect of the analyte on the indicator substance or detection means.

The channel cell may be fabricated by microfabrication methods known to the art, e.g. as exemplified herein, a method comprising forming channels in a silicon microchip, such as by etching grooves into the surface of the silicon microchip and placing a glass cover over the surface. Precision injection molded plastics may also be used for fabrication, as may other materials such as metals. Many procedures suitable for fabrication of these devices are known to the art.

The methods of this invention are designed to be carried out in a device comprising microchannels of a size such that the Reynolds number for flow within the channel is below about 0.1. Reynolds number is the ratio of inertia to viscosity. Low Reynolds number means that inertia is essentially negligible, turbulence is essentially negligible, and, the flow of adjacent streams is laminar, i.e. the streams do not mix except for the diffusion of particles as described above.

The laminar flow channel is long enough to permit small analyte particles to diffuse from the sample stream and have a detectable effect on an indicator substance or detection means, preferably it is at least about 2 mm long. In preferred embodiments of this invention, the channel length is between about 5 mm and about 50 mm. The channel width (diffusion direction) is preferably between about 20 micrometers and about 1 mm. The channel is more preferably made relatively wide, e.g. at least about 200 micrometers, which makes it easier to measure indicator fluorescence with simple optics, and less likely for particles to clog the channel. However, the channel can be made as narrow as possible while avoiding clogging the channel with the particles being used. Narrowing the width of the channel makes diffusion occur more rapidly, and thus detection can be done more rapidly. The channel depth is small enough to allow laminar flow of two streams therein, preferably no greater than about 200 micrometers and more preferably between about 50 micrometers and about 100 micrometers.

In some embodiments, the laminar flow channel may be long enough to allow the indicator and sample streams to reach equilibrium with respect to the analyte particles within the channel. Equilibrium occurs when the maximum amount of smaller particles have diffused into the indicator stream.

The system may also comprise specimen channel and outlet means such as smaller channels for conducting specimen streams from the indicator stream at successive intervals along the length of the laminar flow channel, and means including viewports and fluorescence detectors for measuring changes in an indicator substance in each specimen stream, whereby concentration of the analyte in the sample stream may be determined.

The channel cell system of a preferred embodiment of this invention comprises channel grooves in the form of a "T" or a "Y" having a central trunk and two branches etched into the surface of a silicon microchip, which surface is thereafter covered with a glass sheet. The central groove is formed of the trunk of the "T" or "Y", and the branches are the inlet means in fluid connection with the laminar flow channel for respectively conducting the sample and indicator streams into the laminar flow channel.

Channel cells of this invention may also include multiple inlet branches in fluid connection with the laminar flow channel for conducting a plurality of inlet streams into said channel. These may be arranged in a "candelabra"-like array or may be arranged successively along a "crossbar" for the "T" or the branches of the "Y" configuration, the only constraint being that laminar flow of all the streams must be preserved.

Inlet means include the inlet channels or "branches" and may also include other means such as tubes, syringes, and the like which provide means for injecting feed fluid into the device. Outlet means include collection ports, and/or means for removing fluid from the outlet, including receptacles for the fluid, means inducing flow by capillary action, pressure, gravity, and other means known to the art. Such receptacles may be part of an analytical or detection device.

A method is also provided for detecting the presence of analyte particles in a sample stream, preferably a liquid stream, also comprising larger particles comprising:
 a) conducting said sample stream into a laminar flow channel;
 b) conducting an indicator stream, said indicator stream preferably comprising an indicator substance which indicates the presence of said analyte particles, by a detectable change in property when contacted with particles of said analyte, into said laminar flow channel, whereby said sample stream and said indicator stream flow in adjacent laminar streams in said channel;
 c) allowing analyte particles to diffuse into said indicator stream;
 d) detecting the presence of particles of the analyte in said indicator stream.

The flow rate of the input streams is preferably between about 0.05 and about 50 mm/sec, and is preferably the same for both streams.

The method and system of this invention include determining the concentration of the analyte particles in the sample stream by detecting the position within the laminar flow channel of analyte particles from the sample stream diffusing into the indicator stream causing a detectable change in the indicator stream or in an indicator substance in the indicator stream. The sample stream and the indicator stream may be allowed to reach equilibrium within the laminar flow channel. The location of the boundary of the detection area (i.e. that portion of the indicator stream containing diffused particles at a detectable concentration) with the unaffected indicator stream may be used to provide information about flow speed and/or sample concentration. The physical location of this boundary in the channel for a given analyte stays the same over time as long as the flow speed is constant and the sample unchanged. The location and size of the detection area can be varied by varying flow rate, sample concentration, and/or concentration of an indicator substance so as to optimize the signal for detection.

Information useful for determining the concentration of the analyte particles in the sample stream may be obtained by providing means for conducting specimen streams from the indicator stream at successive intervals along the length of the laminar flow channel, such as smaller channels equipped with viewports as described herein. Detection means such as those listed above are used to measure signals from the indicator stream. Changes in the intensity of the signals from specimen channel to specimen channel may be used to calculate the concentration of analyte particles in the original sample.

The method of one embodiment of this invention includes the use of an indicator substance which is immobilized on a particulate substrate carried within the indicator stream. The indicator substance is preferably a substance which changes in fluorescence or color in the presence of analyte particles, such as a dye, enzyme, or other organic molecule that changes properties as a function of analyte concentration. The term "indicator substance" is also used to refer to polymeric beads, antibodies or the like having dyes or other indicators immobilized thereon. It is not necessary that the indicator stream comprise an indicator substance when detection means such as those directly detecting electrical, chemical or other changes in the indicator stream caused by the analyte particles are used.

Advantages of this system include the fact that analytes can be determined optically in turbid and strongly colored solutions such as blood, without the need for prior filtering or centrifugation; cross-sensitivities of indicator dyes to larger sample components (a common problem) can be avoided; and the indicator can be kept in a solution in which it displays its optimal characteristics (e. g., cross-sensitivities to pH or ionic strength can be suppressed by using strongly buffered solutions). Measurements of the indicator stream at several locations along the channel can compensation for some remaining cross-sensitivities. In addition, the flow channel can be wide, which makes it easy to measure the indicator fluorescence with simple optics. No membrane is needed; the system is less subject to biofouling and clogging than membrane systems. The system is also tunable in that sample or indicator stream concentrations and/or flow rates can be varied to optimize the signal being detected. For example, if a reaction takes about five seconds, the system can be adjusted so that the reaction will be seen in the central portion of the device.

The method can be conducted by a continuous flow-through of sample and indicator streams. The steady-state nature of this method makes longer signal integration times possible.

The sample stream may contain particles larger than the analyte particles which are also sensitive to the indicator substance. These do not diffuse into the indicator stream and thus do not interfere with detection of the analyte.

DETAILED DESCRIPTION

The microscale channel cells of this invention are useful to separate smaller particles from larger particles in a sample stream based on the fact that the diffusion coefficient of a particle is substantially inversely proportional to the size of the particle so that larger particles diffuse more slowly than smaller particles, on the fact that diffusion occurs more quickly at the microscale of this invention than in larger scale separation devices known to the art and on the fact that laminar, non-turbulent flow can be induced in adjacent streams at the microscale.

Figure 1:
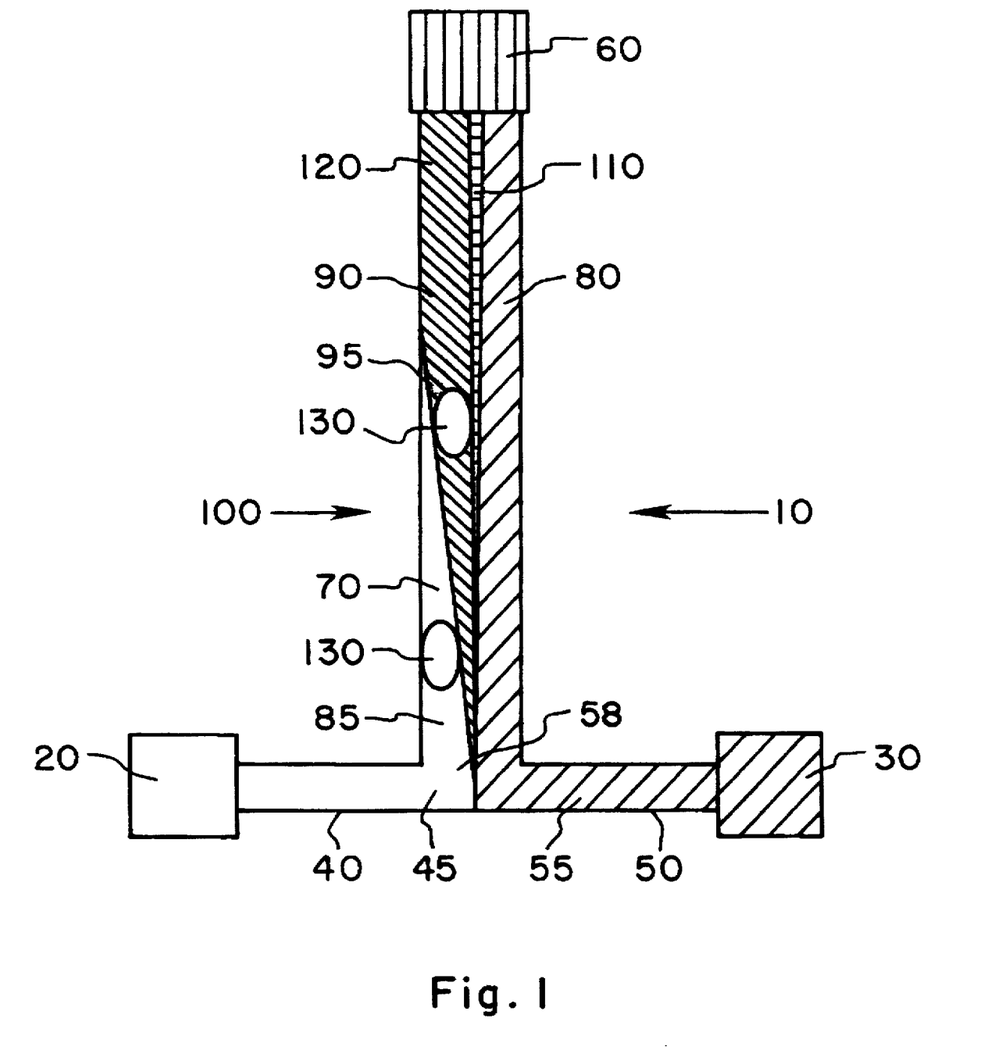
FIG. 1 is a schematic representation of flow and diffusion within the T-sensor channel cell embodiment of this invention.

As shown in FIG. 1, a channel cell in the form of a "T" is provided, referred to herein as T-sensor 10. The device is microfabricated by etching on a silicon microchip. The geometry need not necessarily be a "T," as a "Y." Any angle that can be fabricated will also suffice. As discussed above, there may be a plurality of input channels. It is necessary only that all input channels merge into a single flow channel, and all channels be sufficiently small that the Reynolds number of the system be less than 1 for all operating conditions. The sample containing small molecules of interest, sample stream 80, is brought into the device through sample stream inlet port 30, from whence it flows into sample stream inlet channel 50, where it is referred to as sample inlet stream 55. An indicator stream 70 is brought into indicator stream inlet port 20, from whence it flows into indicator stream inlet channel 40, where it is referred to as indicator inlet stream 45.

Sample inlet stream 55 meets indicator inlet stream 45 at T-joint 58 at the beginning of flow channel 100, and the two streams flow in parallel laminar flow as indicator stream 70 and sample stream 80 to exit port 60. The indicator stream 70 contains an indicator substance such as a dye which reacts to analyte particles in the sample stream 80 by a detectable change in physical properties. Indicator stream 70 is shown in white in FIG. 1. Due to the low Reynolds number in the small flow channel 100, no turbulence-induced mixing occurs and the two streams flow parallel to each other without mixing. However, because of the short distances involved, diffusion does act perpendicular to the flow direction, so sample components (analyte particles) diffuse to the left into indicator stream 70 and eventually become uniformly distributed across the width of flow channel 100 at uniform analyte particle diffusion area 120.

The indicator stream 70 flows into flow channel 100 to form an initial reference area 85 into which analyte particles have not yet diffused. Analyte particles from sample stream 80 diffusing into indicator stream 70 form an analyte detection area 90 where analyte particles create a detectable change in the indicator stream 70, preferably by causing a detectable change in property in an indicator substance within the indicator stream 70. Particles of an indicator substance, e.g. dye particles, may also diffuse into sample stream 80 to form a diffused indicator area 110. If this change in local concentration of the indicator substance is a problem in some applications, its diffusion rate can be made arbitrarily small by immobilization on polymers or beads, e.g. indicator beads 130.

In the T-sensor 10 of FIG. 1, a sample stream 80, e.g. blood, and an indicator stream 70 containing an indicator dye are joined at the intersection of sample stream inlet channel 50 and indicator stream inlet channel 40, with flow channel 100 (i.e., T-joint 58) and flow laminarly next to each other in flow channel 100 until they exit the structure at exit port 60. Small ions such as $H^+$ and $Na^+$ diffuse rapidly across the diameter of flow channel 100, whereas larger ions diffuse only slowly. Larger particles such as large proteins, and the like and blood cells show no significant diffusion within the time the indicator stream 70 and sample stream 80 are in contact with each other. The smaller sample components diffuse more rapidly and equilibrate close to the T-joint 58, whereas larger components equilibrate further up in flow channel 100. Furthermore, as the indicator has a particular half-saturation concentration ($pK_a$, in the case of a pH dye), a front or detection area boundary 95 of indicator dye color or fluorescence change exists as diffusion proceeds up the channel to form detection area 90. In practice the detection area boundary 95 and reference area 85 may form a curved line best seen in FIG. 2. The location and curvature of the front can have its "resting location" adjusted by changing flow speed and channel width to optimize signal size and intensity.

Although this is a flow system, the physical location of the detection area boundary 95 in flow channel 100 for a given analyte stays the same over time as long as the flows are constant and the sample unchanged. Information to determine analyte concentration can be obtained by monitoring indicator signal at uniform analyte particle diffusion area 120 after substantial equilibration, or by noting the position of the front of steepest indicator color change, for example with a multielement detector (see FIG. 3). The analyte detection area 90 and analyte particle diffusion area 120 can be as large as necessary to provide a detectable indicator signal. Similarly reference area 85 can be made to be as large as necessary to provide a detectable reference signal. Adjustments of these areas can be made as described below based on the diffusion coefficients of the analyte and indicator substance, flow rates and channel sizes.

Figure 2:
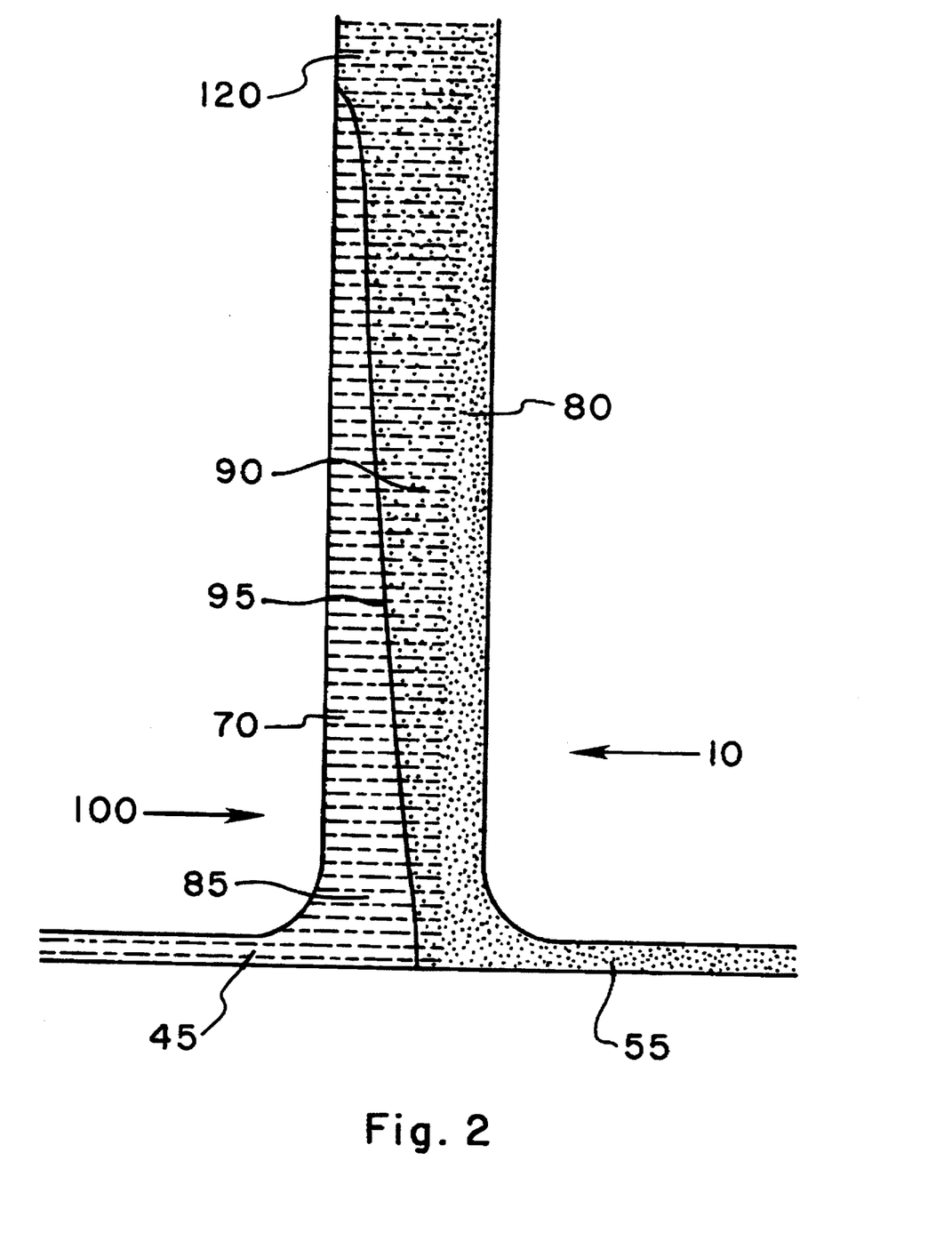
FIG. 2 is a fluorescence micrograph of a T-sensor of this invention in which a buffer solution of pH 9 (right inlet) is flowing into the device, and a weakly buffered indicator dye solution (pH 5) enters from the left. The distinct conversion of the dye from one form to the other as diffusion proceeds is clearly visible.

FIG. 2 shows a schematic representation of a fluorescence microscope photograph of the T-sensor of FIG. 1 featuring an indicator inlet stream 45 which is a weakly buffered indicator dye solution of pH 5, and a sample inlet stream 55 which is a buffer solution of pH 9. The sample stream 80 appears as a clear fluid on the right; the fluid contains $H^+$ analyte particles which are represented by dots. The dashed zone on the left is reference area 85 where analyte particles have not yet diffused into indicator stream 70. The area in the middle represented by dashed lines and dots is analyte detection area 90 where $H^+$ ions from the sample stream 80 have diffused into indicator stream 70 to form detection area 90. The fuzzy right edge of the detection area 90 is caused by dye particles diffusing into the sample stream 80. Uniform analyte particle diffusion area is shown at 120 where the $H^+$ ions are uniformly diffused The strongest signal is in the middle of detection area 90.

Figure 3:
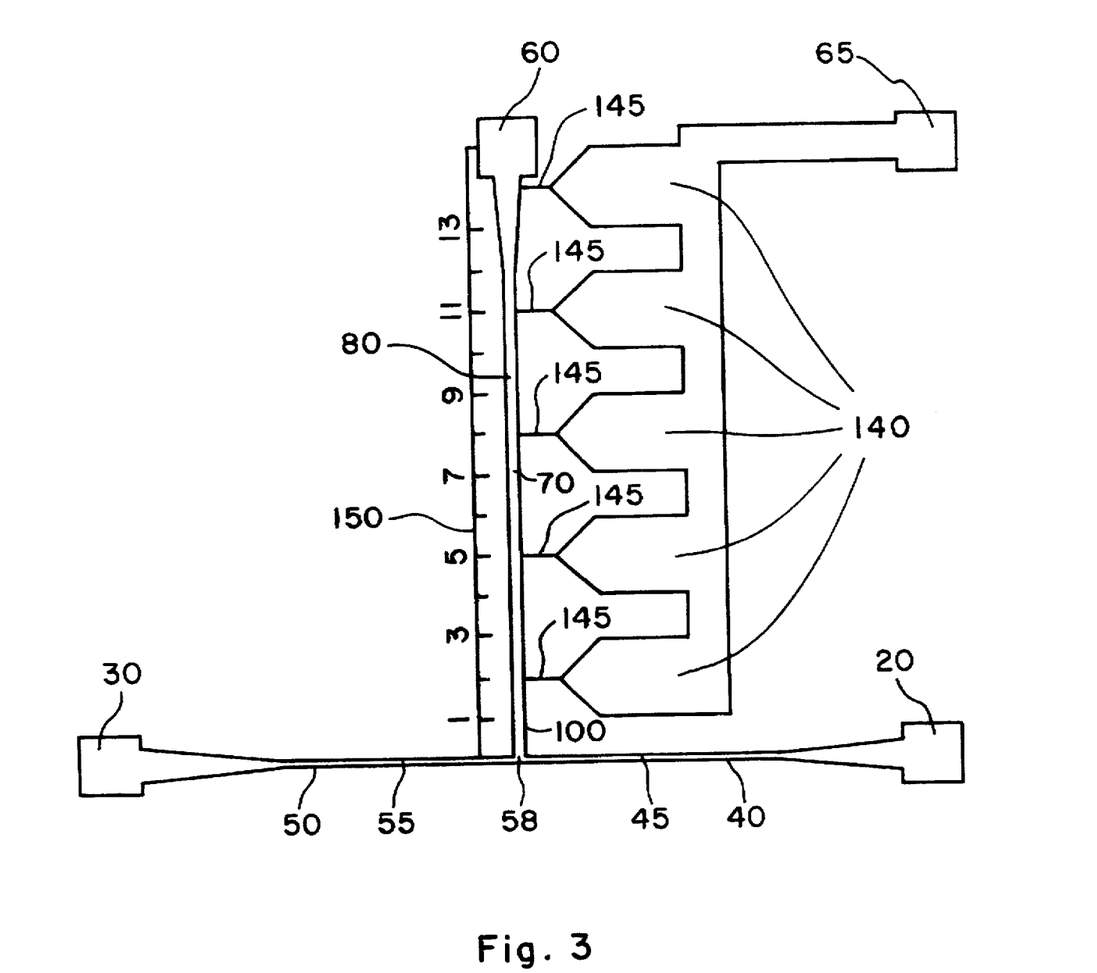
FIG. 3 shows the layout of the viewport-T-sensor embodiment of this invention. In this embodiment the indicator stream comes from the right T-leg, and is a solution of indicator dye in a low ionic strength buffer of pH 9. The sample stream, which is introduced from the left, is a 0.15M buffer solution of pH 5. Several portions of the indicator stream which contains the indicator dye are continuously taken out of the channel as specimen streams at various locations.

FIG. 3 shows another embodiment of the T-sensor channel cell device of this invention having multiple specimen channels and viewports spaced along the length of the flow channel. In FIG. 3 an indicator inlet stream 45 enters from the right (rather than the left as in FIGS. 1 and 2) at indicator stream inlet port 20. A solution of indicator dye in a low ionic strength buffer of pH 9 is used. A sample inlet stream 55 which is a 0.15M buffer solution of pH 5, enters from the left at sample stream inlet port 30. The concentration of the dye is only about 10% of the dye concentration used in FIG. 2. The indicator and sample streams, 45 and 55 respectively, flow along indicator stream inlet channel and sample stream inlet channel 40 and 50 respectively, to meet at T-joint 58 and flow laminarly together along flow channel 100. Specimen streams 145 from indicator stream 70 which contain the indicator dye are continuously taken out of flow channel 100 at various locations. These specimen streams 145 flow through widenings which serve as viewports 140. Due to the size of the viewports 140 (several square millimeters), the fluorescence intensity can be easily monitored through a fluorescence microscope, or directly with a photodetector.

The viewport closest to T-joint 58 contains mainly undisturbed dye solution, whereas the viewport closest to exit port 60 contains the sample stream 80 completely equilibrated with the indicator stream 70. The viewports in between contain the indicator stream 70 in various degrees of equilibration with the sample components. The closer to T-joint 58, the more likely the viewport is to contain only small ions from the sample. A fluorescence micrograph of the viewports shows that the color in the viewport closest to T-joint 58 is the red color of the base form of the undisturbed indicator dye, whereas the yellow-green color of the viewports closest to exit port 60 represent the acid form of the dye, after the pH of the indicator stream 70 was altered from basic to acid when diffusion-based equilibration has been reached.

The viewport T-sensor of FIG. 3 lends itself to simple referencing techniques. The integral fluorescence intensity of each viewport at one or more wavelengths can easily be measured through a fluorescence microscope, or directly, with photodiodes. In the easiest case, with an indicator dye showing no cross-sensitivity to other sample components, the intensity ratio between selected viewports gives a measurement value largely independent of dye concentration and excitation light intensity. Measuring at more than one viewport increases the redundancy and therefore the measurement accuracy.

In cases of cross-sensitivity of the indicator to larger sample components (e.g. larger biomolecules such as albumin), this interference can be referenced out by comparing the ratios of the different viewports. The viewports closer to T-joint 58 will contain mainly smaller sample components, whereas the viewports further up flow channel 100 will also contain larger particles.

The channel cells of this invention may be formed by any techniques known to the art, for example by etching the flow channels onto the horizontal surface of a silicon wafer and placing a lid, preferably of an optically clear material such as glass or a silicone rubber sheet, on the etched substrate. Other means for manufacturing the channel cells of this invention include using silicon structures or other materials to make a template for molding the device in plastic, micromachining, and other techniques known to the art. The use of precision injection molded plastics to form the devices is also contemplated. Microfabrication techniques are known to the art, and more particularly described below.

In a preferred embodiment of this invention, channel cells of this invention have hydrophilic surfaces to facilitate flow of liquid therein and allow operation of the device without the necessity for pressurization. The substrate may be treated by means known to the art following fabrication of the channels to render it hydrophilic. The lid is also preferably treated to render it hydrophilic. Means for applying pressure to the flow of the feed fluids through the device may also be provided. Such means may be provided at the feed inlets and/or the outlet (e.g. as vacuum exerted by chemical or mechanical means). Means for applying such pressure are known to the art, for example as described in Shoji, S. and Esashi, M. (1994), "Microflow devices and systems," J. Micromechanics and Microengineering, 4:157–171, and include the use of a column of water or other means of applying water pressure, electroendoosmotic forces, optical forces, gravitational forces, and surface tension forces. Pressures from about $10^{-6}$ psi to about 10 psi may be used, depending on the requirements of the system. Preferably about $10^{-3}$ psi is used. Most preferred pressures are between about 2 mm and about 100 mm of water pressure.

An example of an embodiment using multiple streams is a channel cell having three inlet streams flowing in laminar flow wherein the middle stream is a reagent stream. For example, the sample stream may be blood, the middle stream glucose oxidase, and the third stream an indicator stream containing pH sensitive dye. As glucose particles diffuse through the reagent stream they are changed to gluconic acid which is detected by a pH-sensitive dye when the gluconic acid molecules diffuse into the indicator stream. Other examples of multiple-stream systems include systems having several sample streams with analyte at different concentrations for calibration of the detection means. Indicator streams not adjacent to the sample streams may also be used as control streams.

The indicator stream can be measured by the detection means before and after diffusion of particles into the stream has taken place, and such measurements as well as the rate of change of the indicator stream along its length can be used to assay analyte concentration. In addition, multiple detection means of different types can be used to measure the indicator stream. Field effects which are ion or chemical sensitive can be measured at different locations in the device.

The channel cells of this invention and the channels therein can be sized as determined by the size of the particles desired to be detected. As is known in the art, the diffusion coefficient for the analyte particles is inversely related to the size of the particle. Once the diffusion coefficient for the particles desired to be detected is known, the contact time of the two streams, size of the central channel, relative volumes of the streams, pressure and velocities of the streams can be adjusted to achieve the desired diffusion pattern.

Fluid dynamic behavior is directly related to the Reynolds number of the flow. In microdevices, if the velocity decreases as the channel length (where the device is assumed to work in a fixed time at all scales), then the Reynolds number varies in proportion to the square of the length. As devices are miniaturized, the Reynolds number is inevitably reduced.

The Reynolds number is the ratio of inertial forces to viscous forces. As the Reynolds number is reduced, flow patterns depend more on viscous effects and less on inertial effects. Below a certain Reynolds number, e.g. 0.1 (based on lumen size for a system of channels with bends and lumen size changes), inertial effects can essentially be ignored. The microfluidic devices of this invention do not require inertial effects to perform their tasks, and therefore have no inherent limit on their miniaturization due to Reynolds number effects. Applicants' channel cell designs, while significantly different from previous reported designs, operate in this range. These microfluidic devices of this invention require laminar, non-turbulent flow and are designed according to the foregoing principles to produce flows having low Reynolds numbers.

The devices of the preferred embodiment of this invention are capable of analyzing a sample of a size between about 0.01 microliters and about 20 microliters within a few seconds, e.g. within about three to five seconds. They also may be reused. Clogging is minimized and reversible. The sizes and velocities of 100 µm wide and 100 µm/s, for example, indicate a Reynolds number ($R_e = \rho l v / \eta$) of about $10^{-2}$ so that the fluid is in a regime where viscosity dominates over inertia.

The magnitude of the pressure drop needed to obtain an average velocity, v, of a fluid with absolute viscosity, $\eta$, and density, $\rho$, through a circular channel (length, l, diameter, d) can be calculated from Poiseuille's Law (Batchelor, G. K., *An Introduction to Fluid Dynamics*, Cambridge Univ. Press 1967).

$$\frac{P}{l} = \frac{32 \eta v}{d^2}$$

Using v=100 µm/sec and d=100 µm, we get a pressure drop equivalent to about 0.3 mm of $H_2O$ per cm of channel length. Since Poiseuille's equation is only strictly valid for circular flow channels and the channels of this invention are substantially rectangular in cross-section it can be considered only as an approximate relation between the variables represented.

When a liquid is introduced into a device there is at first an effective pressure, $P_{eff} = P_o + P_{st}$, equal to the sum of the applied pressure, $P_o$, and a pressure due to the surface tension.

$$P_{st} = \frac{\gamma \cos \Theta}{r}$$

$P_{st}$ is a function of the surface tension of the fluid, $\gamma$, the contact angle of the fluid with the surface, $\Theta$, and the radius of curvature of the fluid surface, r.

For hydrophilic surfaces, $\cos \Theta$ is close to 1, and for small channels no applied pressure is needed to wet the device. This is referred to as "wetting by capillary action." However, once the device is completely wet, one has to worry about the surface tension at the exit area. The radius of curvature of the fluid in the exit area can be adjusted, e.g., to several millimeters, so that the pressure due to the surface tension is negligible.

With a channel width of 100 µm, $P_{st}$ is about 1 cm of $H_2O$, so surface tension on the exit channel is significant. However, using an etchant such as EPW F-Etch as described below, which attacks the {100} planes of silicon, means that the corners as etched are not sharp. This results in a gradual widening of the channel which reduces the effect of the surface tension.

By adjusting the configuration of the channels in accordance with the principles discussed above to provide an appropriate channel length, flow velocity and contact time between the sample stream and the indicator stream, the size of the particles remaining in the sample stream and diffusing into the indicator stream can be controlled. The contact time required can be calculated as a function of the diffusion coefficient of the particle D and the distance d over which the particle must diffuse by $t = d^2/D$. Particles or molecules that have diffusion coefficients larger than D will diffuse into the indicator stream, and particles or molecules having a diffusion coefficient substantially smaller than D will not. If the diffusion coefficient of the larger particles is about ten times smaller than D, the indicator stream should be entirely free of the large particles.

EXAMPLES

Example 1

Fabrication of Channel Cell

A two-mask level process was used to fabricate a channel cell of this invention on a silicon wafer. The channel cell had a flow channel 400 micrometers wide and 20 mm long. The "branches" or crossbar of the "T" comprising the inlet channels was a groove 30 mm long and 200 micrometers wide. Channel depth was 50 micrometers.

The first mask level defined the inlets and outlet ports, which were etched completely through the wafer to the rear side of the silicon. The second level defined the fluid transport channels.

Four inch chrome masks were made to these specifications by Photo Sciences, Inc. (Torrance, Calif.) and 3" wafers ({100}, n-type) with 500 nm of $SiO_2$ grown on them were used.

Wafers were cleaned in a Piranha bath ($H_2SO_4$ and $H_2O_2$) (2:1) before processing. A primer (HMDS spun on at 3000 rpm) was used to enhance photoresist adhesion. About one µm of AZ-1370-SF (Hoechst) photoresist was deposited by spin coating (3000 rpm), and this was followed by a soft bake (30 min at 90° C.).

A contact aligner was used to align and expose wafers. Exposure time was varied to yield best results. No post-exposure bake was done. Wafers were developed in AZ-351 (diluted 4:1) (Hoechst) for one minute and rinsed in DI water. Blue tack tape (Semiconductor Equipment Corporation, Moorpark, Calif.) was applied to the backsides of the wafers to protect the oxide from the oxide etch.

The wafers were immersed in a buffered oxide etch (BOE, 10:1 HF (49%) and $NH_4F$ (10%)) for eleven minutes to completely etch away the unprotected oxide. The blue tack tape was removed by hand, and the photoresist was removed in an acetone rinse.

Silicon etching was done in a mixture of ethylene-diamine, pyro-catechol, and water (EPW F-etch as described in Reisman, A., et al. (1979) *J. Electrochem. Soc.* 126:1406–1415) set up in a reflux boiling flask. This etch attacks the {100} planes of silicon at a rate of about 100 µm an hour. Fluid attachment ports were etched in the first step for about three hours. Photoresist was again applied, and the mask containing flow channels between fluid ports and the barrier region was exposed. The wafers were developed and etched in this second step for about one hour.

After final processing, the wafers were once again cleaned in a Piranha bath and rinsed in DI water. They were then diced into individual devices about 1 cm by 1 cm.

Anodic bonding according to Wallis, G. and Pomerantz, D. I. (1969) *J. Appl. Physics* 40:3946–3949, was used to attach Pyrex glass to the silicon devices. One inch square pieces of Pyrex glass (100 µm thickness) from Esco Products Inc. (Oak Ridge, N.J.) were used. First, the silicon and Pyrex glass were immersed in a solution of $H_2O_2$, $NH_4OH$, and $H_2O$ (1:4:6) heated to 50° C. This process removes any organic matter on the surfaces and also makes the surfaces hydrophilic. After 20 minutes in this solution, the silicon and Pyrex were rinsed with DI water and dried. Anodic bonding was done at 400° C. with 400 V applied between the glass and the silicon.

Example 2

Fluorescence Color Changes with pH

Five 0.01M HEPES Buffer solutions, with pH 7.2, 7.4, 7.6, 7.8 and 8.0 were prepared from analytical grade chemicals (Aldrich). The resulting solutions were used consecutively as sample streams. The analyte in question in this experiment is $H^+$ or $OH^-$. 1 mg of the fluorescent pH indicator dye carboxy— 1 ml of a 0.0001M HEPES Buffer of pH 7.0. The resulting solution was used as the indicator stream.

The T-sensor channel cell was attached to the stage of a microscope so that the joint of the T-sensor was in the view field of the objective. The inlet ports and the outlet port were connected to injector loops and to upright tubes which were filled with water so that there was a pressure difference of 30 mm water column between the inlet ports and the outlet port. Both inlet ports were exposed to identical pressure so that the two streams joined in the middle of the T-joint, and were flowing parallel to the outlet port. One injector loop was filed with indicator dye solution, the other loop was filled with one of the sample solutions. The loops contained enough volume to operate the device for roughly one hour.

After both injection loops were allowed to flow into the T-sensor, and after 1 min of equilibration and flushing time, photographs were taken through a camera attachment on the microscope. The excitation filter center wavelength was 480 nm, the emission filter was a longpass 510 nm filter.

The experiment yielded photographs in which the color of the interaction zone between the indicator stream and the sample stream was a function of the pH of the sample stream. The color changed from red over orange to yellow as the pH decreased from 8.0 to 7.2. Computer-enhanced images showed the color of the indicator stream per se to be yellow, and the interaction zone between the streams to range from red to orange, whereas the colorless sample stream appeared black. By color mapping, numeric values are assigned to the different colors which are used to calibrate the system. Alternatively, light intensity change is measured at two wavelengths, thereby measuring the decrease of the red portion and the increase of the yellow portion of the spectrum with decreasing pH.

We claim:

1. A method for detecting the presence of analyte particles in a sample stream also comprising larger particles comprising:
   a) conducting said sample stream into a laminar flow channel;
   b) conducting an indicator stream into said laminar flow channel, whereby said sample stream and said indicator stream flow in adjacent laminar streams in said channel;
   c) allowing analyte particles to diffuse into said indicator stream;
   d) detecting the presence of analyte particles in said indicator stream.

2. The method of claim 1 wherein said indicator and sample streams are liquid streams.

3. The method of claim 1 wherein said indicator stream comprises an indicator substance which indicates the presence of said analyte particles by a detectable change in property when contacted with particles of said analyte, and said detecting step comprises detecting a change in property of said indicator substance.

4. The method of claim 3 wherein said indicator substance is immobilized on a particulate substrate carried within said indicator stream.

5. The method of claim 3 wherein said indicator substance is a substance which changes in fluorescence in the presence of said analyte particles.

6. The method of claim 3 wherein said indicator substance is sensitive not only to said analyte particles, but also to particles in said sample stream larger than said analyte particles.

7. The method of claim 1 wherein comprising conducting multiple sample streams into laminar flow in said flow channel.

8. The method of claim 1 comprising conducting multiple indicator streams into laminar flow in said flow channel.

9. The method of claim 1 comprising also conducting reference or calibration streams into laminar flow in said flow channel.

10. The method of claim 1 wherein specimen streams are conducted from the indicator stream at successive intervals along the length of said laminar flow channel and changes in the indicator stream measured in each specimen stream and compared with the changes measured in each other specimen stream, whereby concentration of the analyte in the sample stream is determinable.

11. The method of claim 1 wherein analyte concentration in said sample stream is determined within at most about three seconds.

12. A channel cell system for detecting the presence of analyte particles in a sample stream also comprising larger particles comprising:
   a) a laminar flow channel;
   b) at least two inlet means in fluid connection with said laminar flow channel for respectively conducting into said laminar flow channel (1) an indicator stream and (2) said sample stream;
   c) wherein said laminar flow channel has a depth sufficiently small to allow laminar flow of said streams and a length sufficient to allow particles of said analyte to diffuse into said indicator stream to the substantial exclusion of said larger particles in said sample stream to form a detection area;
   d) outlet means for conducting said streams out of said laminar flow channel to form a single mixed stream.

13. The system of claim 12 wherein said indicator stream comprises an indicator substance which indicates the presence of said analyte particles by a detectable change in property when contacted with said analyte particles.

14. The system of claim 12 also comprising external detecting means for detecting changes in the indicator stream as a result of contact with analyte particles.

15. The system of claim 14 wherein said external detection means comprise a fluorescence detector.

16. The system of claim 13 comprising an analyte stream comprising a liquid carrier and substrate particles on which said indicator substance is immobilized in a liquid carrier introduced into one of said inlet means.

17. The system of claim 12 comprising means for conducting specimen streams from the indicator stream at successive intervals along the length of said laminar flow channel and means for measuring signals from the indicator stream in each specimen stream whereby concentration of the analyte in the sample stream may be determined.

18. A system for detecting the presence of particles of an analyte in a liquid sample stream also comprising larger particles, said system comprising a channel cell fabricated by etching channel grooves in the form of a "T" or a "Y" having a central trunk and two branches into the surface of a silicon microchip and covering said grooves with glass, said channel cell comprising:

a) a laminar flow channel formed of the trunk of said "T" or "Y";

b) two inlet means comprising branches of said "T" or "Y" in fluid connection with said laminar flow channel for respectively conducting into said laminar flow channel (1) an indicator stream comprising an indicator substance which indicates the presence of said analyte particles by a detectable change in property when contacted with said analyte particles, and (2) said sample stream;

c) wherein said laminar flow channel has a depth sufficiently small such that parallel laminar flow of said streams occurs therein, and a length sufficient that particles of said analyte diffuse into said indicator stream to the substantial exclusion of said larger particles in said sample stream to form a detection area, and said indicator and sample streams reach equilibrium within said laminar flow channel;

d) outlet means for conducting said streams out of said laminar flow channel to form a single mixed stream.

19. The system of claim 18 also comprising channel means for conducting specimen streams from the indicator stream at successive intervals along the length of said laminar flow channel and viewport means for measuring signals from the indicator substance in each specimen stream whereby concentration of the analyte in the sample stream is determinable.

* * * * *